(12) United States Patent
Richardson et al.

(10) Patent No.: US 9,902,960 B2
(45) Date of Patent: Feb. 27, 2018

(54) ANTISENSE OLIGONUCLEOTIDE COMPOSITIONS

(71) Applicant: UNIVERSITY OF GREENWICH, London (GB)

(72) Inventors: Simon Clifford Wainwright Richardson, London (GB); Paul Douglas Remane Dyer, London (GB); John Carlton Mitchell, London (GB)

(73) Assignee: UNIVERSITY OF GREENWICH, London (GB)

(*) Notice: Subject to any disclaimer, the term of this patent is extended or adjusted under 35 U.S.C. 154(b) by 0 days.

(21) Appl. No.: 14/899,631

(22) PCT Filed: Jun. 23, 2014

(86) PCT No.: PCT/GB2014/051918
§ 371 (c)(1),
(2) Date: Dec. 18, 2015

(87) PCT Pub. No.: WO2014/203008
PCT Pub. Date: Dec. 24, 2014

(65) Prior Publication Data
US 2016/0152984 A1 Jun. 2, 2016

(30) Foreign Application Priority Data
Jun. 21, 2013 (GB) .................................. 1311057.2

(51) Int. Cl.
*C12N 15/11* (2006.01)
*C12N 15/113* (2010.01)

(52) U.S. Cl.
CPC ........ *C12N 15/1131* (2013.01); *C12N 15/111* (2013.01); *C12N 15/113* (2013.01); *C12N 2310/11* (2013.01); *C12N 2310/13* (2013.01); *C12N 2310/3513* (2013.01); *C12N 2310/3519* (2013.01); *C12N 2320/32* (2013.01)

(58) Field of Classification Search
CPC ............ C12N 15/1131; C12N 2310/11; C12N 2310/3513
See application file for complete search history.

(56) References Cited

U.S. PATENT DOCUMENTS

| 6,835,810 | B2* | 12/2004 | Hwu | ..................... | C07K 14/005 530/300 |
| 2009/0093026 | A1* | 4/2009 | Dowdy | .................. | C12N 15/111 435/69.7 |
| 2013/0011837 | A1* | 1/2013 | Dickinson | ............ | C12Q 1/6806 435/6.11 |

FOREIGN PATENT DOCUMENTS

| WO | 9528494 A1 | 10/1995 |
| WO | 9723236 | 7/1997 |
| WO | 9859065 A1 | 12/1998 |
| WO | 03082346 A1 | 10/2003 |
| WO | 03083476 A1 | 10/2003 |
| WO | 2006091233 A2 | 8/2006 |
| WO | WO2013088446 A1 * | 6/2013 |

OTHER PUBLICATIONS

Gramlich et al. J Drug Target 2013: 21:662-674.*
Pan, et al; "Structure and Function of the Zinc-II Binding Site Withing the DNA-Binding Domain of the GAL4 Transcription Factor," Proceedings of the National Academy of Sciences of the United States of America, vol. 86, No. 9, 1989, pp. 3145-3149.
Gaur, et al; "Delivery of nucleic acid into mammalian cells by anthrax toxin," Biochemical and Biophysical Research Communications, Oct. 11, 2002, vol. 297, No. 5, pp. 1121-1127.
Krantz, et al; "Acid-induced Unfolding of the Amino-terminal Domains of the Lethal and Edema Factors of Anthrax Toxin," Journal of Molecular Biology, 2004, pp. 1-18.
Scholz, et al; "Therapeutic plasmid DNA versus siRNA delivery: Common and different tasks for synthetic carriers," Journal of Controlled Release, 2012, vol. 161, pp. 554-565.
Abrami, et al; "Membrane insertion of anthrax protective antigen and cytoplasmic delivery of lethal factor occur at different stages of the endocytic pathway," The Journal of Cell Biology, Aug. 30, 2004, vol. 166, No. 5, pp. 645-651.
Dyer, et al; "Delivery of biologics to select organelles—the role of biologically active polymers," Expert Opin. Drug Deliv., 2011, vol. 8, No. 4, pp. 403-407.
International Search Report for PCT/GB2014/051918 dated Jan. 5, 2015.
Gu et al. "Stochastic Sensing of Organic Analytes by a Pore-Forming Protein Containing a Molecular Adapter." Nature 398: 686-690; Apr. 22, 1999.
Yacyshyn, et al. "Double blind, placebo control trial of the remission inducing and steroid sparing properties of an ICAM-1 antisense oligodeoxynucleotide, alicaforsen (ISIS 2302), in active steroid dependent Crohn's disease." Gut 2002 51: 30-36; Nov. 6, 2001.
Dias et al. "Antisense Oligonucleotides: Basic Concepts and Mechanisms." Molecular Cancer Therapeutics 1: 347-355; Mar. 2002.
Astriab-Fisher et al. "Increased uptake of antisense oligonucleotides by delivery as double stranded complexes." Biochemical Pharmacology 68: 403-407; Mar. 19, 2004.

(Continued)

*Primary Examiner* — Brian A Whiteman
(74) *Attorney, Agent, or Firm* — Heslin Rothenberg Farley and Mesiti, PC

(57) ABSTRACT

The present invention relates to antisense oligonucleotide (ASO) compositions and particularly to compositions and methods for the cytosolic delivery of antisense oligonucleotides (ASOs). Hybrid ASOs, part single-stranded and part double-stranded, are provided, hybridizing to form a double-stranded region that can non-covalently bond to nucleic-acid-binding protein regions. In this way, ASO::protein complexes may be produced that facilitate delivery of antisense DNA into target cells. Such complexes may be used to down-regulate gene expression in cells.

14 Claims, 10 Drawing Sheets

(56) References Cited

OTHER PUBLICATIONS

Young, et al. "Anthrax Toxin: Receptor Binding, Internalization, Pore Formation, and Translocation." Annual Review of Biochemistry 76: 243-265; Mar. 2, 2007.
Wright et al. "Effective delivery of antisense peptide nucleic acid oligomers into cells by anthrax protective antigen." Biochemical and Biophysical Research Communications 376: 200-205; Aug. 21, 2008.

* cited by examiner

SEQ ID No: 1

ATGGAACGCAACAAAACTCAGGAGGAACACCTGAAAGAGATCATGAAACACATTGTTAAAAT
CGAGGTGAAAGGCGAAGAAGCGGTTAAAAAGGAGGCTGCCGAAAAGCTGCTGGAGAAGGT
ACCGTCTGATGTGCTGGAAATGTATAAAGCGATTGGTGGCAAAATCTACATCGTGGATGGTGAT
ATTACCAAACACATCTCCCTGGAAGCACTGAGCGAAGACAAGAAGAAGATCAAAGATATCTAC
GGCAAGGACGCGCTGCTGCACGAGCATTACGTTTACGCAAAAGAAGGTTACGAACCGGTGCT
GGTTATCCAGTCCAGCGAGGATTACGTCGAAAATACGGAAAAAGCTCTGAACGTATATTACGA
AATTGGTAAAATCCTGTCTCGTGACATTCTGAGCAAAATTAACCAACCTTATCAGAAGTTCCTG
GACGTTCTGAACACCATCAAAAACGCTTCTGACTCCGACGGCCAGGACCTGCTGTTCACTAAT
CAGCTGAAAGAACATCCGACCGATTTCTCTGTAGAATTCCTGGAACAGAACTCTAACGAGGTC
CAAGAAGTTTTTGCCAAAGCATTCGCGTACTACATCGAGCCGCAGCATCGCGACGTGCTGCAG
CTGTACGCTCCAGAAGCCTTCAACTATATGGACAAATTCAATGAACAAGAAATCAACCTGTCTA
TGAAACTGCTGTCCTCCATCGAACAGGCTTGCGATATCTGTCGTCTGAAGAAACTGAAATGCTC
TAAAGAAAAACCGAAATGCGCGAAATGCCTGAAAAACAACTGGGAATGTCGCTATTCCCCTAA
AACCAAACGTTCTCCACTGACCCGTGCGCACCTGACCGAAGTAGAATCCCGTCTGGAACGTCT
GGAGCAGCTGTTTCTGCTGATTTTCCCGCGTGAAGACCTGGACATGATCCTGAAAATGGATAG
CCTGCAGGATATCAAAGCACTGCTGACCGGTCTGTTTGTGCAGGACAACGTCAACAAAGACG
CTGTTACTGATCGCCTGGCGAGCGTTGAAACTGATATGCCGCTGACCCTGCGTCAGCACCGTAT
CTCCGCAACGAGCTCCAGCGAAGAATCTAGCAACAAAGGTCAGCGCCAGCTGACCGTTAGC

Figure 6

SEQ ID No: 2

MERNKTQEEHLKEIMKHIVKIEVKGEEAVKKEAAEKLLEKVPSDVLEMYKAIGGKIYIVDGDITKHI
SLEALSEDKKKIKDIYGKDALLHEHYVYAKEGYEPVLVIQSSEDYVENTEKALNVYYEIGKILSRDILSK
INQPYQKFLDVLNTIKNASDSDGQDLLFTNQLKEHPTDFSVEFLEQNSNEVQEVFAKAFAYYIEPQ
HRDVLQLYAPEAFNYMDKFNEQEINLS

Figure 7

SEQ ID No: 3

MKLLSSIEQACDICRLKKLKCSKEKPKCAKCLKNNWECRYSPKTKRSPLTRAHLTEVESRLERLEQLF
LLIFPREDLDMILKMDSLQDIKALLTGLFVQDNVNKDAVTDRLASVETDMPLTLRQHRISATSSSEE
SSNKGQRQLTVS

Figure 8

SEQ ID No: 4

ATGTAAACCGATTCCGAACCCGCTGCTGGGCCTGGACTCTACTATGGAACGCAACAAAACTCA
GGAGGAACACCTGAAAGAGATCATGAAACACATTGTTAAAATCGAGGTGAAAGGCGAAGAA
GCGGTTAAAAAGGAGGCTGCCGAAAAGCTGCTGGAGAAGGTACCGTCTGATGTGCTGGAAA
TGTATAAAGCGATTGGTGGCAAAATCTACATCGTGGATGGTGATATTACCAAACACATCTCCCT
GGAAGCACTGAGCGAAGACAAGAAGAAGATCAAAGATATCTACGGCAAGGACGCGCTGCTG
CACGAGCATTACGTTTACGCAAAAGAAGGTTACGAACCGGTGCTGGTTATCCAGTCCAGCGA
GGATTACGTCGAAAATACGGAAAAAGCTCTGAACGTATATTACGAAATTGGTAAAATCCTGTCT
CGTGACATTCTGAGCAAAATTAACCAACCTTATCAGAAGTTCCTGGACGTTCTGAACACCATCA
AAAACGCTTCTGACTCCGACGGCCAGGACCTGCTGTTCACTAATCAGCTGAAAGAACATCCGA
CCGATTTCTCTGTAGAATTCCTGGAACAGAACTCTAACGAGGTCCAAGAAGTTTTTGCCAAAG
CATTCGCGTACTACATCGAGCCGCAGCATCGCGACGTGCTGCAGCTGTACGCTCCAGAAGCCT
TCAACTATATGGACAAATTCAATGAACAAGAAATCAACCTGTCTATGAAACTGCTGTCCTCCATC
GAACAGGCTTGCGATATCTGTCGTCTGAAGAAACTGAAATGCTCTAAAGAAAAACCGAAATGC
GCGAAATGCCTGAAAAACAACTGGGAATGTCGCTATTCCCCTAAAACCAAACGTTCTCCACTG
ACCCGTGCGCACCTGACCGAAGTAGAATCCCGTCTGGAACGTCTGGAGCAGCTGTTTCTGCTG
ATTTTCCCGCGTGAAGACCTGGACATGATCCTGAAAATGGATAGCCTGCAGGATATCAAAGCA
CTGCTGACCGGTCTGTTTGTGCAGGACAACGTCAACAAAGACGCTGTTACTGATCGCCTGGCG
AGCGTTGAAACTGATATGCCGCTGACCCTGCGTCAGCACCGTATCTCCGCAACGAGCTCCAGC
GAAGAATCTAGCAACAAAGGTCAGCGCCAGCTGACCGTTAGCCACCACCATCACCACCACTAA
GG

Figure 9

SEQ ID No: 5

MGKPIPNPLLGLDSTMERNKTQEEHLKEIMKHIVKIEVKGEEAVKKEAAEKLLEKVPSDVLEMYKA
IGGKIYIVDGDITKHISLEALSEDKKKIKDIYGKDALLHEHYVYAKEGYEPVLVIQSSEDYVENTEKAL
NVYYEIGKILSRDILSKINQPYQKFLDVLNTIKNASDSDGQDLLFTNQLKEHPTDFSVEFLEQNSNE
VQEVFAKAFAYYIEPQHRDVLQLYAPEAFNYMDKFNEQEINLSMKLLSSIEQACDICRLKKLKCSKE
KPKCAKCLKNNWECRYSPKTKRSPLTRAHLTEVESRLERLEQLFLLIFPREDLDMILKMDSLQDIKAL
LTGLFVQDNVNKDAVTDRLASVETDMPLTLRQHRISATSSSEESSNKGQRQLTVSHHHHHH

Figure 10

SEQ ID No: 6

ATGAGAGGATCGCATCACCATCACCATCACGGATCCGAAGTTAAACAGGAGAACCGGTTATTAAAT
GAATCAGAATCAAGTTCCCAGGGGTTACTAGGATACTATTTTAGTGATTTGAATTTTCAAGCACCCAT
GGTGGTTACCTCTTCTACTACAGGGGATTTATCTATTCCTAGTTCTGAGTTAGAAAATATTCCATCGG
AAAACCAATATTTTCAATCTGCTATTTGGTCAGGATTTATCAAAGTTAAGAAGAGTGATGAATATACA
TTTGCTACTTCCGCTGATAATCATGTAACAATGTGGGTAGATGACCAAGAAGTGATTAATAAAGCTTC
TAATTCTAACAAAATCAGATTAGAAAAAGGAAGATTATATCAAATAAAAATTCAATATCAACGAGAA
AATCCTACTGAAAAAGGATTGGATTTCAAGTTGTACTGGACCGATTCTCAAAATAAAAAAGAAGTG
ATTTCTAGTGATAACTTACAATTGCCAGAATTAAAACAAAAATCTTCGAACTCAAGAAAAAAGCGAA
GTACAAGTGCTGGACCTACGGTTCCAGACCGTGACAATGATGGAATCCCTGATTCATTAGAGGTAG
AAGGATATACGGTTGATGTCAAAAATAAAAGAACTTTTCTTTCACCATGGATTTCTAATATTCATGAA
AAGAAAGGATTAACCAAATATAAATCATCTCCTGAAAAATGGAGCACGGCTTCTGATCCGTACAGTG
ATTTCGAAAAGGTTACAGGACGGATTGATAAGAATGTATCACCAGAGGCAAGACACCCCCTTGTGG
CAGCTTATCCGATTGTACATGTAGATATGGAGAATATTATTCTCTCAAAAAATGAGGATCAATCCACA
CAGAATACTGATAGTCAAACGAGAACAATAAGTAAAAATACTTCTACAAGTAGGACACATACTAGTG
AAGTACATGGAAATGCAGAAGTGCATGCGTCGTTCTTTGATATTGGTGGGAGTGTATCTGCAGGAT
TTAGTAATTCGAATTCAAGTACGGTCGCAATTGATCATTCACTATCTCTAGCAGGGGAAAGAACTTG
GGCTGAAACAATGGGTTTAAATACCGCTGATACAGCAAGATTAAATGCCAATATTAGATATGTAAATA
CTGGGACGGCTCCAATCTACAACGTGTTACCAACGACTTCGTTAGTGTTAGGAAAAAATCAAACAC
TCGCGACAATTAAAGCTAAGGAAAAACCAATTAAGTCAAATACTTGCACCTAATAATTATTATCCTTCT
AAAAACTTGGCGCCAATCGCATTAAATGCACAAGACGATTTCAGTTCTACTCCAATTACAATGAATT
ACAATCAATTTCTTGAGTTAGAAAAAACGAAACAATTAAGATTAGATACGGATCAAGTATATGGGAA
TATAGCAACATACAATTTTGAAAATGGAAGAGTGAGGGTGGATACAGGCTCGAACTGGAGTGAAG
TGTTACCGCAAATTCAAGAAACAACTGCACGTATCATTTTTAATGGAAAAGATTTAAATCTGGTAGA
AAGGCGGATAGCGGCGGTTAATCCTAGTGATCCATTAGAAACGACTAAACCGGATATGACATTAAA
AGAAGCCCTTAAAATAGCATTTGGATTTAACGAACCGAATGGAAACTTACAATATCAAGGGAAAGA
CATAACCGAATTTGATTTTAATTTCGATCAACAAACATCTCAAAATATCAAGAATCAGTTAGCGGAAT
TAAACGCAACTAACATATATACTGTATTAGATAAAATCAAATTAAATGCAAAAATGAATATTTTAATAA
GAGATAAACGTTTTCATTATGATAGAAATAACATAGCAGTTGGGGCGGATGAGTCAGTAGTTAAGG
AGGCTCATAGAGAAGTAATTAATTCGTCAACAGAGGGATTATTGTTAAATATTGATAAGGATATAAG
AAAAATATTATCAGGTTATATTGTAGAAATTGAAGATACTGAAGGGCTTAAAGAAGTTATAAATGAC
AGATATGATATGTTGAATATTTCTAGTTTACGGCAAGATGGAAAAACATTTATAGATTTTAAAAAATAT
AATGATAAATTACCGTTATATATAAGTAATCCCAATTATAAGGTAAATGTATATGCTGTTACTAAAGAAA
ACACTATTATTAATCCTAGTGAGAATGGGGATACTAGTACCAACGGGATCAAGAAAATTTTAATCTTT
TCTAAAAAAGGCTATGAGATAGGATGA

Figure 11

SEQ ID No: 7

MRGSHHHHHHGSEVKQENRLLNESESSSQGLLGYYFSDLNFQAPMVVTSSTTGDLSIPSSELENI
PSENQYFQSAIWSGFIKVKKSDEYTFATSADNHVTMWVDDQEVINKASNSNKIRLEKGRLYQIKI
QYQRENPTEKGLDFKLYWTDSQNKKEVISSDNLQLPELKQKSSNSRKKRSTSAGPTVPDRDNDGI
PDSLEVEGYTVDVKNKRTFLSPWISNIHEKKGLTKYKSSPEKWSTASDPYSDFEKVTGRIDKNVSP
EARHPLVAAYPIVHVDMENIILSKNEDQSTQNTDSQTRTISKNTSTSRTHTSEVHGNAEVHASFF
DIGGSVSAGFSNSNSSTVAIDHSLSLAGERTWAETMGLNTADTARLNANIRYVNTGTAPIYNVLP
TTSLVLGKNQTLATIKAKENQLSQILAPNNYYPSKNLAPIALNAQDDFSSTPITMNYNQFLELEKTK
QLRLDTDQVYGNIATYNFENGRVRVDTGSNWSEVLPQIQETTARIIFNGKDLNLVERRIAAVNPS
DPLETTKPDMTLKEALKIAFGFNEPNGNLQYQGKDITEFDFNFDQQTSQNIKNQLAELNATNIYT
VLDKIKLNAKMNILIRDKRFHYDRNNIAVGADESVVKEAHREVINSSTEGLLLNIDKDIRKILSGYIV
EIEDTEGLKEVINDRYDMLNISSLRQDGKTFIDFKKYNDKLPLYISNPNYKVNVYAVTKENTIINPSE
NGDTSTNGIKKILIFSKKGYEIG

Figure 12

SEQUENCE LISTING

<160> NUMBER OF SEQ ID NOS: 21

<210> SEQ ID NO 1
<211> LENGTH: 1131
<212> TYPE: DNA
<213> ORGANISM: Artificial sequence
<220> FEATURE:
<223> OTHER INFORMATION: Derived from more than one source

<400> SEQUENCE: 1

```
atggaacgca acaaaactca ggaggaacac ctgaaagaga tcatgaaaca cattgttaaa      60
atcgaggtga aaggcgaaga agcggttaaa aaggaggctg ccgaaaagct gctggagaag     120
gtaccgtctg atgtgctgga aatgtataaa gcgattggtg gcaaaatcta catcgtggat     180
ggtgatatta ccaaacacat ctccctggaa gcactgagcg aagacaagaa gaagatcaaa     240
gatatctacg gcaaggacgc gctgctgcac gagcattacg tttacgcaaa agaaggttac     300
gaaccggtgc tggttatcca gtccagcgag gattacgtcg aaaatacgga aaaagctctg     360
aacgtatatt acgaaattgg taaaatcctg tctcgtgaca ttctgagcaa aattaaccaa     420
ccttatcaga agttcctgga cgttctgaac accatcaaaa acgcttctga ctccgacggc     480
caggacctgc tgttcactaa tcagctgaaa gaacatccga ccgatttctc tgtagaattc     540
ctggaacaga actctaacga ggtccaagaa gttttttgcca agcattcgc gtactacatc     600
gagccgcagc atcgcgacgt gctgcagctg tacgctccag aagccttcaa ctatatggac     660
aaattcaatg aacaagaaat caacctgtct atgaaactgc tgtcctccat cgaacaggct     720
tgcgatatct gtcgtctgaa gaaactgaaa tgctctaaag aaaaaccgaa atgcgcgaaa     780
tgcctgaaaa acaactggga atgtcgctat tcccctaaaa ccaaacgttc tccactgacc     840
cgtgcgcacc tgaccgaagt agaatcccgt ctggaacgtc tggagcagct gtttctgctg     900
atttccccgc gtgaagacct ggacatgatc ctgaaaatgg atagcctgca ggatatcaaa     960
gcactgctga ccggtctgtt tgtgcaggac aacgtcaaca agacgctgt tactgatcgc    1020
ctggcgagcg ttgaaactga tatgccgctg accctgcgtc agcaccgtat ctccgcaacg    1080
agctccagcg aagaatctag caacaaaggt cagcgccagc tgaccgttag c             1131
```

<210> SEQ ID NO 2
<211> LENGTH: 230
<212> TYPE: PRT
<213> ORGANISM: Bacillus anthracis

<400> SEQUENCE: 2

```
Met Glu Arg Asn Lys Thr Gln Glu Glu His Leu Lys Glu Ile Met Lys
1               5                   10                  15
His Ile Val Lys Ile Glu Val Lys Gly Glu Glu Ala Val Lys Lys Glu
            20                  25                  30
Ala Ala Glu Lys Leu Leu Glu Lys Val Pro Ser Asp Val Leu Glu Met
        35                  40                  45
Tyr Lys Ala Ile Gly Gly Lys Ile Tyr Ile Val Asp Gly Asp Ile Thr
    50                  55                  60
Lys His Ile Ser Leu Glu Ala Leu Ser Glu Asp Lys Lys Ile Lys
65                  70                  75                  80
Asp Ile Tyr Gly Lys Asp Ala Leu Leu His Glu His Tyr Val Tyr Ala
                85                  90                  95
Lys Glu Gly Tyr Glu Pro Val Leu Val Ile Gln Ser Ser Glu Asp Tyr
            100                 105                 110
```

```
Val Glu Asn Thr Glu Lys Ala Leu Asn Val Tyr Tyr Glu Ile Gly Lys
        115                 120                 125

Ile Leu Ser Arg Asp Ile Leu Ser Lys Ile Asn Gln Pro Tyr Gln Lys
    130                 135                 140

Phe Leu Asp Val Leu Asn Thr Ile Lys Asn Ala Ser Asp Ser Asp Gly
145                 150                 155                 160

Gln Asp Leu Leu Phe Thr Asn Gln Leu Lys Glu His Pro Thr Asp Phe
                165                 170                 175

Ser Val Glu Phe Leu Glu Gln Asn Ser Asn Glu Val Gln Glu Val Phe
            180                 185                 190

Ala Lys Ala Phe Ala Tyr Tyr Ile Glu Pro Gln His Arg Asp Val Leu
        195                 200                 205

Gln Leu Tyr Ala Pro Glu Ala Phe Asn Tyr Met Asp Lys Phe Asn Glu
    210                 215                 220

Gln Glu Ile Asn Leu Ser
225                 230

<210> SEQ ID NO 3
<211> LENGTH: 147
<212> TYPE: PRT
<213> ORGANISM: Saccharomyces cerevisiae

<400> SEQUENCE: 3

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser
145

<210> SEQ ID NO 4
<211> LENGTH: 1197
<212> TYPE: DNA
<213> ORGANISM: Artificial sequence
<220> FEATURE:
<223> OTHER INFORMATION: Derived from more than one source

<400> SEQUENCE: 4
atgggtaaac cgattccgaa cccgctgctg ggcctggact ctactatgga acgcaacaaa      60
actcaggagg aacacctgaa agagatcatg aaacacattg ttaaaatcga ggtgaaaggc     120
gaagaagcgt taaaaaagga ggctgccgaa aagctgctgg agaaggtacc gtctgatgtg     180
ctggaaatgt ataaagcgat tggtggcaaa atctacatcg tggatggtga tattaccaaa     240
```

```
cacatctccc tggaagcact gagcgaagac aagaagaaga tcaaagatat ctacggcaag    300
gacgcgctgc tgcacgagca ttacgtttac gcaaaagaag gttacgaacc ggtgctggtt    360
atccagtcca gcgaggatta cgtcgaaaat acggaaaaag ctctgaacgt atattacgaa    420
attggtaaaa tcctgtctcg tgacattctg agcaaaatta accaacctta tcagaagttc    480
ctggacgttc tgaacaccat caaaaacgct tctgactccg acggccagga cctgctgttc    540
actaatcagc tgaaagaaca tccgaccgat ttctctgtag aattcctgga acagaactct    600
aacgaggtcc aagaagtttt tgccaaagca ttcgcgtact acatcgagcc gcagcatcgc    660
gacgtgctgc agctgtacgc tccagaagcc ttcaactata tggacaaatt caatgaacaa    720
gaaatcaacc tgtctatgaa actgctgtcc tccatcgaac aggcttgcga tatctgtcgt    780
ctgaagaaac tgaaatgctc taagaaaaaa ccgaaatgcg cgaaatgcct gaaaacaac     840 tgggaatgtc gctattcccc taaaaccaaa cgttctccac tgacccgtgc gcacctgacc    900
gaagtagaat cccgtctgga acgtctggag cagctgtttc tgctgatttt cccgcgtgaa    960
gacctggaca tgatcctgaa aatggatagc ctgcaggata tcaaagcact gctgaccggt   1020
ctgtttgtgc aggacaacgt caacaaagac gctgttactg atcgcctggc gagcgttgaa   1080
actgatatgc cgctgaccct gcgtcagcac cgtatctccg caacgagctc cagcgaagaa   1140
tctagcaaca aggtcagcg ccagctgacc gttagccacc accatcacca ccactaa      1197
```

<210> SEQ ID NO 5
<211> LENGTH: 398
<212> TYPE: PRT
<213> ORGANISM: Artificial sequence
<220> FEATURE:
<223> OTHER INFORMATION: Derived from more than one source

<400> SEQUENCE: 5

```
Met Gly Lys Pro Ile Pro Asn Pro Leu Leu Gly Leu Asp Ser Thr Met
1               5                   10                  15

Glu Arg Asn Lys Thr Gln Glu Glu His Leu Lys Glu Ile Met Lys His
            20                  25                  30

Ile Val Lys Ile Glu Val Lys Gly Glu Glu Ala Val Lys Lys Glu Ala
        35                  40                  45

Ala Glu Lys Leu Leu Glu Lys Val Pro Ser Asp Val Leu Glu Met Tyr
    50                  55                  60

Lys Ala Ile Gly Gly Lys Ile Tyr Ile Val Asp Gly Asp Ile Thr Lys
65                  70                  75                  80

His Ile Ser Leu Glu Ala Leu Ser Glu Asp Lys Lys Ile Lys Asp
                85                  90                  95

Ile Tyr Gly Lys Asp Ala Leu Leu His Glu His Tyr Val Tyr Ala Lys
            100                 105                 110

Glu Gly Tyr Glu Pro Val Leu Val Ile Gln Ser Ser Glu Asp Tyr Val
        115                 120                 125

Glu Asn Thr Glu Lys Ala Leu Asn Val Tyr Tyr Glu Ile Gly Lys Ile
    130                 135                 140

Leu Ser Arg Asp Ile Leu Ser Lys Ile Asn Gln Pro Tyr Gln Lys Phe
145                 150                 155                 160

Leu Asp Val Leu Asn Thr Ile Lys Asn Ala Ser Asp Ser Asp Gly Gln
                165                 170                 175

Asp Leu Leu Phe Thr Asn Gln Leu Lys Glu His Pro Thr Asp Phe Ser
            180                 185                 190
```

Val Glu Phe Leu Glu Gln Asn Ser Asn Glu Val Gln Glu Val Phe Ala
            195                 200                 205

Lys Ala Phe Ala Tyr Tyr Ile Glu Pro Gln His Arg Asp Val Leu Gln
        210                 215                 220

Leu Tyr Ala Pro Glu Ala Phe Asn Tyr Met Asp Lys Phe Asn Glu Gln
225                 230                 235                 240

Glu Ile Asn Leu Ser Met Lys Leu Leu Ser Ile Glu Gln Ala Cys
                245                 250                 255

Asp Ile Cys Arg Leu Lys Lys Leu Cys Ser Lys Glu Lys Pro Lys
            260                 265                 270

Cys Ala Lys Cys Leu Lys Asn Asn Trp Glu Cys Arg Tyr Ser Pro Lys
        275                 280                 285

Thr Lys Arg Ser Pro Leu Thr Arg Ala His Leu Thr Glu Val Glu Ser
    290                 295                 300

Arg Leu Glu Arg Leu Glu Gln Leu Phe Leu Leu Ile Phe Pro Arg Glu
305                 310                 315                 320

Asp Leu Asp Met Ile Leu Lys Met Asp Ser Leu Gln Asp Ile Lys Ala
                325                 330                 335

Leu Leu Thr Gly Leu Phe Val Gln Asp Asn Val Asn Lys Asp Ala Val
            340                 345                 350

Thr Asp Arg Leu Ala Ser Val Glu Thr Asp Met Pro Leu Thr Leu Arg
        355                 360                 365

Gln His Arg Ile Ser Ala Thr Ser Ser Ser Glu Glu Ser Ser Asn Lys
    370                 375                 380

Gly Gln Arg Gln Leu Thr Val Ser His His His His His
385                 390                 395

<210> SEQ ID NO 6
<211> LENGTH: 2244
<212> TYPE: DNA
<213> ORGANISM: Bacillus anthracis

<400> SEQUENCE: 6
atgagaggat cgcatcacca tcaccatcac ggatccgaag ttaaacagga gaaccggtta      60
ttaaatgaat cagaatcaag ttcccagggg ttactaggat actattttag tgatttgaat     120
tttcaagcac ccatggtggt tacctcttct actacagggg attatctat tcctagttct      180 gagttagaaa atattccatc ggaaaaccaa tattttcaat ctgctatttg gtcaggattt     240
atcaaagtta agaagagtga tgaatataca tttgctactt ccgctgataa tcatgtaaca    300
atgtgggtag atgaccaaga agtgattaat aaagcttcta attctaacaa atcagatta     360 gaaaaggaa gattatatca ataaaaatt caatatcaac gagaaaatcc tactgaaaaa      420
ggattggatt tcaagttgta ctggaccgat tctcaaaata aaaagaagt gatttctagt      480 gataacttac aattgccaga attaaaacaa aaatcttcga actcaagaaa aaagcgaagt     540
acaagtgctg gacctacggt tccagaccgt gacaatgatg aatcccctga ttcattagag     600
gtagaaggat atacggttga tgtcaaaaat aaaagaactt ttcttttcacc atggatttct    660 aatattcatg aaaagaaagg attaaccaaa tataaatcat ctcctgaaaa atggagcacg    720
gcttctgatc cgtacagtga tttcgaaaag gttacaggac ggattgataa gaatgtatca    780
ccagaggcaa gacaccccct tgtggcagct tatccgattg tacatgtaga tatggagaat    840
attattctct caaaaaatga ggatcaatcc acacagaata ctgatagtca acgagaaaca    900
ataagtaaaa atacttctac aagtaggaca catactagtg aagtacatgg aaatgcagaa    960

```
gtgcatgcgt cgttctttga tattggtggg agtgtatctg caggatttag taattcgaat    1020
tcaagtacgg tcgcaattga tcattcacta tctctagcag gggaaagaac ttgggctgaa    1080
acaatgggtt taaataccgc tgatacagca agattaaatg ccaatattag atatgtaaat    1140
actgggacgg ctccaatcta caacgtgtta ccaacgactt cgttagtgtt aggaaaaaat    1200
caaacactcg cgacaattaa agctaaggaa aaccaattaa gtcaaatact tgcacctaat    1260
aattattatc cttctaaaaa cttggcgcca atcgcattaa atgcacaaga cgatttcagt    1320
tctactccaa ttacaatgaa ttacaatcaa tttcttgagt tagaaaaaac gaaacaatta    1380
agattagata cggatcaagt atatgggaat atagcaacat acaattttga aaatggaaga    1440
gtgagggtgg atacaggctc gaactggagt gaagtgttac cgcaaattca agaaacaact    1500
gcacgtatca tttttaatgg aaaagattta aatctggtag aaaggcggat agcggcggtt    1560
aatcctagtg atccattaga aacgactaaa ccggatatga cattaaaaga agcccttaaa    1620
atagcatttg gatttaacga accgaatgga aacttacaat atcaagggaa agacataacc    1680
gaatttgatt ttaatttcga tcaacaaaca tctcaaaata tcaagaatca gttagcggaa    1740
ttaaacgcaa ctaacatata tactgtatta gataaaatca aattaaatgc aaaaatgaat    1800
attttaataa gagataaacg ttttcattat gatagaaata acatagcagt tggggcggat    1860
gagtcagtag ttaaggaggc tcatagagaa gtaattaatt cgtcaacaga gggattattg    1920
ttaaatattg ataaggatat aagaaaaata ttatcaggtt atattgtaga aattgaagat    1980
actgaagggc ttaaagaagt tataaatgac agatatgata tgttgaatat ttctagttta    2040
cggcaagatg gaaaaacatt tatagatttt aaaaaatata atgataaatt accgttatat    2100
ataagtaatc ccaattataa ggtaaatgta tatgctgtta ctaaagaaaa cactattatt    2160
aatcctagtg agaatgggga tactagtacc aacgggatca agaaaatttt aatcttttct    2220
aaaaaaggct atgagatagg atga                                          2244
```

<210> SEQ ID NO 7
<211> LENGTH: 747
<212> TYPE: PRT
<213> ORGANISM: Bacillus anthracis

<400> SEQUENCE: 7

```
Met Arg Gly Ser His His His His His His Gly Ser Glu Val Lys Gln
1               5                   10                  15

Glu Asn Arg Leu Leu Asn Glu Ser Glu Ser Ser Ser Gln Gly Leu Leu
            20                  25                  30

Gly Tyr Tyr Phe Ser Asp Leu Asn Phe Gln Ala Pro Met Val Val Thr
        35                  40                  45

Ser Ser Thr Thr Gly Asp Leu Ser Ile Pro Ser Glu Leu Glu Asn
    50                  55                  60

Ile Pro Ser Glu Asn Gln Tyr Phe Gln Ser Ala Ile Trp Ser Gly Phe
65                  70                  75                  80

Ile Lys Val Lys Lys Ser Asp Glu Tyr Thr Phe Ala Thr Ser Ala Asp
                85                  90                  95

Asn His Val Thr Met Trp Val Asp Asp Gln Glu Val Ile Asn Lys Ala
            100                 105                 110

Ser Asn Ser Asn Lys Ile Arg Leu Glu Lys Gly Arg Leu Tyr Gln Ile
        115                 120                 125

Lys Ile Gln Tyr Gln Arg Glu Asn Pro Thr Glu Lys Gly Leu Asp Phe
    130                 135                 140
```

-continued

```
Lys Leu Tyr Trp Thr Asp Ser Gln Asn Lys Lys Glu Val Ile Ser Ser
145                 150                 155                 160

Asp Asn Leu Gln Leu Pro Glu Leu Lys Gln Lys Ser Ser Asn Ser Arg
                165                 170                 175

Lys Lys Arg Ser Thr Ser Ala Gly Pro Thr Val Pro Asp Arg Asp Asn
            180                 185                 190

Asp Gly Ile Pro Asp Ser Leu Glu Val Glu Gly Tyr Thr Val Asp Val
        195                 200                 205

Lys Asn Lys Arg Thr Phe Leu Ser Pro Trp Ile Ser Asn Ile His Glu
    210                 215                 220

Lys Lys Gly Leu Thr Lys Tyr Lys Ser Pro Glu Lys Trp Ser Thr
225                 230                 235                 240

Ala Ser Asp Pro Tyr Ser Asp Phe Glu Lys Val Thr Gly Arg Ile Asp
                245                 250                 255

Lys Asn Val Ser Pro Glu Ala Arg His Pro Leu Val Ala Ala Tyr Pro
            260                 265                 270

Ile Val His Val Asp Met Glu Asn Ile Ile Leu Ser Lys Asn Glu Asp
        275                 280                 285

Gln Ser Thr Gln Asn Thr Asp Ser Gln Thr Arg Thr Ile Ser Lys Asn
    290                 295                 300

Thr Ser Thr Ser Arg Thr His Thr Ser Glu Val His Gly Asn Ala Glu
305                 310                 315                 320

Val His Ala Ser Phe Phe Asp Ile Gly Gly Ser Val Ser Ala Gly Phe
                325                 330                 335

Ser Asn Ser Asn Ser Ser Thr Val Ala Ile Asp His Ser Leu Ser Leu
            340                 345                 350

Ala Gly Glu Arg Thr Trp Ala Glu Thr Met Gly Leu Asn Thr Ala Asp
        355                 360                 365

Thr Ala Arg Leu Asn Ala Asn Ile Arg Tyr Val Asn Thr Gly Thr Ala
    370                 375                 380

Pro Ile Tyr Asn Val Leu Pro Thr Thr Ser Leu Val Leu Gly Lys Asn
385                 390                 395                 400

Gln Thr Leu Ala Thr Ile Lys Ala Lys Glu Asn Gln Leu Ser Gln Ile
                405                 410                 415

Leu Ala Pro Asn Asn Tyr Tyr Pro Ser Lys Asn Leu Ala Pro Ile Ala
            420                 425                 430

Leu Asn Ala Gln Asp Asp Phe Ser Ser Thr Pro Ile Thr Met Asn Tyr
        435                 440                 445

Asn Gln Phe Leu Glu Leu Glu Lys Thr Lys Gln Leu Arg Leu Asp Thr
    450                 455                 460

Asp Gln Val Tyr Gly Asn Ile Ala Thr Tyr Asn Phe Glu Asn Gly Arg
465                 470                 475                 480

Val Arg Val Asp Thr Gly Ser Asn Trp Ser Glu Val Leu Pro Gln Ile
                485                 490                 495

Gln Glu Thr Thr Ala Arg Ile Ile Phe Asn Gly Lys Asp Leu Asn Leu
            500                 505                 510

Val Glu Arg Arg Ile Ala Ala Val Asn Pro Ser Asp Pro Leu Glu Thr
        515                 520                 525

Thr Lys Pro Asp Met Thr Leu Lys Glu Ala Leu Lys Ile Ala Phe Gly
    530                 535                 540

Phe Asn Glu Pro Asn Gly Asn Leu Gln Tyr Gln Gly Lys Asp Ile Thr
545                 550                 555                 560

Glu Phe Asp Phe Asn Phe Asp Gln Gln Thr Ser Gln Asn Ile Lys Asn
```

-continued

```
                565                 570                 575
Gln Leu Ala Glu Leu Asn Ala Thr Asn Ile Tyr Thr Val Leu Asp Lys
            580                 585                 590
Ile Lys Leu Asn Ala Lys Met Asn Ile Leu Ile Arg Asp Lys Arg Phe
        595                 600                 605
His Tyr Asp Arg Asn Asn Ile Ala Val Gly Ala Asp Glu Ser Val Val
    610                 615                 620
Lys Glu Ala His Arg Glu Val Ile Asn Ser Ser Thr Glu Gly Leu Leu
625                 630                 635                 640
Leu Asn Ile Asp Lys Asp Ile Arg Lys Ile Leu Ser Gly Tyr Ile Val
                645                 650                 655
Glu Ile Glu Asp Thr Glu Gly Leu Lys Glu Val Ile Asn Asp Arg Tyr
            660                 665                 670
Asp Met Leu Asn Ile Ser Ser Leu Arg Gln Asp Gly Lys Thr Phe Ile
        675                 680                 685
Asp Phe Lys Lys Tyr Asn Asp Lys Leu Pro Leu Tyr Ile Ser Asn Pro
    690                 695                 700
Asn Tyr Lys Val Asn Val Tyr Ala Val Thr Lys Glu Asn Thr Ile Ile
705                 710                 715                 720
Asn Pro Ser Glu Asn Gly Asp Thr Ser Thr Asn Gly Ile Lys Lys Ile
                725                 730                 735
Leu Ile Phe Ser Lys Lys Gly Tyr Glu Ile Gly
            740                 745

<210> SEQ ID NO 8
<211> LENGTH: 48
<212> TYPE: DNA
<213> ORGANISM: Artificial sequence
<220> FEATURE:
<223> OTHER INFORMATION: Synthetic

<400> SEQUENCE: 8
aatttgtttg ttgaggctaa tgcatgccgg ctgctctgat gccggcat            48

<210> SEQ ID NO 9
<211> LENGTH: 48
<212> TYPE: DNA
<213> ORGANISM: Artificial sequence
<220> FEATURE:
<223> OTHER INFORMATION: Synthetic

<400> SEQUENCE: 9
aatttgtttg ttgaggctaa tgcatgccgg catcagagca gccggcat            48

<210> SEQ ID NO 10
<211> LENGTH: 49
<212> TYPE: DNA
<213> ORGANISM: Artificial sequence
<220> FEATURE:
<223> OTHER INFORMATION: Derived from more than one source

<400> SEQUENCE: 10
ggtcgtctgc tgagctttct atgcatgccg gctgctctga tgccggcat           49

<210> SEQ ID NO 11
<211> LENGTH: 49
<212> TYPE: DNA
<213> ORGANISM: Artificial sequence
<220> FEATURE:
<223> OTHER INFORMATION: Derived from more than one source
```

<400> SEQUENCE: 11
ggtcgtctgc tgagctttct atgcatgccg gcatcagagc agccggcat         49

<210> SEQ ID NO 12
<211> LENGTH: 50
<212> TYPE: DNA
<213> ORGANISM: Artificial sequence
<220> FEATURE:
<223> OTHER INFORMATION: Derived from more than one source

<400> SEQUENCE: 12
ggtgctcttc atcttgttgg tatgcatgcc ggctgctctg atgccggcat         50

<210> SEQ ID NO 13
<211> LENGTH: 50
<212> TYPE: DNA
<213> ORGANISM: Artificial sequence
<220> FEATURE:
<223> OTHER INFORMATION: Derived from more than one source

<400> SEQUENCE: 13
ggtgctcttc atcttgttgg tatgccggca tcagagcagc cggcatgcat         50

<210> SEQ ID NO 14
<211> LENGTH: 25
<212> TYPE: DNA
<213> ORGANISM: Artificial sequence
<220> FEATURE:
<223> OTHER INFORMATION: Derived from more than one source

<400> SEQUENCE: 14
atgccggcat cagagcagcc ggcat         25

<210> SEQ ID NO 15
<211> LENGTH: 25
<212> TYPE: DNA
<213> ORGANISM: Artificial sequence
<220> FEATURE:
<223> OTHER INFORMATION: Derived from more than one source

<400> SEQUENCE: 15
atgccggctg ctctgatgcc ggcat         25

<210> SEQ ID NO 16
<211> LENGTH: 48
<212> TYPE: DNA
<213> ORGANISM: Artificial sequence
<220> FEATURE:
<223> OTHER INFORMATION: Derived from more than one source

<400> SEQUENCE: 16
tacggccgac gagactacgg ccgtacgtaa atttgtttgt tgaggcta         48

<210> SEQ ID NO 17
<211> LENGTH: 48
<212> TYPE: DNA
<213> ORGANISM: Artificial sequence
<220> FEATURE:
<223> OTHER INFORMATION: Derived from more than one source

<400> SEQUENCE: 17
atgccggcat cagagcagcc ggcatgctaa atttgtttgt tgaggcta         48

<210> SEQ ID NO 18
<211> LENGTH: 19

```
<212> TYPE: DNA
<213> ORGANISM: Artificial sequence
<220> FEATURE:
<223> OTHER INFORMATION: Derived from more than one source

<400> SEQUENCE: 18
aatttgtttg ttgaggcta                                              19

<210> SEQ ID NO 19
<211> LENGTH: 17
<212> TYPE: DNA
<213> ORGANISM: Artificial sequence
<220> FEATURE:
<223> OTHER INFORMATION: Derived from more than one source

<400> SEQUENCE: 19
cggctgctct gatgccg                                                17

<210> SEQ ID NO 20
<211> LENGTH: 17
<212> TYPE: DNA
<213> ORGANISM: Artificial sequence
<220> FEATURE:
<223> OTHER INFORMATION: Derived from more than one source

<400> SEQUENCE: 20
cggcatcaga gcagccg                                                17

<210> SEQ ID NO 21
<211> LENGTH: 21
<212> TYPE: DNA
<213> ORGANISM: Artificial sequence
<220> FEATURE:
<223> OTHER INFORMATION: Derived from more than one source

<400> SEQUENCE: 21
ggtgctcttc atcttgttgg a                                           21
```

ANTISENSE OLIGONUCLEOTIDE COMPOSITIONS

CROSS REFERENCE TO RELATED APPLICATIONS

This application is a U.S. National Phase filing under 35 U.S.C. § 371 of International Application PCT/GB2014/051918, filed Jun. 23, 2014, and published as WO 2014/203008 on Dec. 24, 2014. PCT/GB2014/051918 claimed benefit of priority from Great Britain Application 1311057.2, filed Jun. 21, 2013. The entire contents of each of the prior applications are hereby incorporated herein by reference.

The present invention relates to antisense oligonucleotide (ASO) compositions and particularly to compositions and methods for the cytosolic delivery of antisense oligonucleotides (ASOs). Hybrid ASOs, part single-stranded and part double-stranded, are provided, hybridising to form a double-stranded region that can non-covalently bond to nucleic-acid-binding protein regions. In this way, ASO::protein complexes may be produced that facilitate delivery of antisense DNA into target cells. Such complexes may be used to down-regulate gene expression in cells.

Antisense oligonucleotides have been approved by the FDA for use as antivirals, for the treatment of cytomegalovirus-mediated retinitis and chronic ulcerative colitis (Roehr, 1998; Yacychyn et al., 1998). ASOs are comprised of segments of single-stranded DNA, or analogues thereof, that are designed to hybridise to a messenger RNA (mRNA) transcript, derived from a specific gene. The mRNA::ASO hybrids so formed may be degraded by RNAse H. In an organism infected with a virus, the genetic material of the virus enters specific cells in order to replicate, a process requiring the translation of virus-specific mRNA. By treating an infected cell with an antisense oligonucleotide specific for virus mRNA, it is possible to prevent the expression of a target viral gene and to block the viral life cycle.

An important factor in the effectiveness of antisense oligonucleotide treatment is the bioavailability of the oligonucleotides (Biroccio et al., 2003). Bioavailability can be limited by the inability of antisense oligonucleotides to penetrate the plasma membrane or endomembrane system of cells. Since the targets of antisense oligonucleotides (e.g., mRNA) are located within the cytosol of a cell, the oligonucleotides need to be able to traverse cell membranes before they can access the cytosol.

One way to address this problem of cytosolic access of antisense oligonucleotides is to administer the treatment locally rather than systemically, and in particular, to administer the antisense oligonucleotide into a discrete pharmacokinetic compartment, raising the local concentration of the antisense oligonucleotide. For example, an antisense oligonucleotide treatment of cytomegalovirus-mediated retinitis involves administering fomivirsen (Vitravene®) into a discrete pharmacokinetic compartment by intravitreal injection. However, cytosolic access i.e., access of the antisense oligonucleotides to their target mRNA, remains a substantial limitation, even after intravitreal administration (Lysik and Wu-Pong, 2003). Other approaches to antisense oligonucleotide intracellular delivery may involve: mechanical and electrical cell damage to the cell membrane, polymeric and lipid carriers (known to non-specifically destabilise membranes), or viral vectors. However, these and similar approaches have not proved to be safe or reliable in the clinic and have not resulted (to date) in any delivery technologies licensed for antisense products in the market place.

The present invention aims to provide compositions and methods for use in a system for the down-regulation of one or more genes within a cell by means of a novel arrangement of an active antisense sequence (e.g., of single-stranded DNA) flanking a partially overlapping second oligonucleotide strand that forms a binding site that can bind to a proteinaceous, nucleic-acid-binding domain. We term these partly single- and partly double-stranded nucleotides, "ASO hybrids". Unexpectedly, we have discovered and have shown empirically (unpublished data):

1) That ASO hybrids can show an equivalent antisense activity profile to the control single-stranded antisense oligonucleotide in a cell-free assay, for example at an ASO concentration of 30 pMol.
2) That ASO hybrids bind to a nucleic-acid-binding domain (such as *S. cerevisiae* GAL4) to form a complex without requiring a polycationic affinity handle (such as poly(L-lysine), used previously (Gaur et al., 2002; WO97/23236)) or other covalent chemical conjugation methods.
3) That if, in an ASO hybrid complex (for example, GAL4::ASO) the nucleic-acid-binding domain is fused to attenuated lethal factor domain 1 (from *Bacillus anthracis*, i.e., LFn), this supramolecular assembly can pass through a pore derived from a bacterial virulence factor (*Bacillus anthracis* PA63). This is unexpected as it is reported that passage through the PA pore requires the structural disassembly of cargo (molten globular transition) (Zornetta et al., 2010). For a supramolecular complex to transit into the cytosol via the PA pore, molten globular transition of the cargo, i.e., a transition from an ordered structure to a random coil, must not be taking place. Again this transition has been shown without the use of a polycationic affinity handle (such as poly(L-lysine) (Gaur et al., 2002: WO97/23236)).

It is a particular aim of the present invention to provide a conjugation strategy to enable compositions of antisense oligonucleotides to cross a cell membrane. In this way, antisense oligonucleotides can be delivered to the cytosol of a cell providing direct access to RNA or DNA targets within the cytosol (such as viral mRNA transcripts) via the described antisense-to-protein conjugation strategy.

In one aspect, the present invention provides an antisense oligonucleotide composition comprising a pair of antisense oligonucleotides, wherein the two antisense oligonucleotides hybridise to give at least one single-stranded antisense sequence and at least one double-stranded protein-binding sequence. Preferably the composition further comprises a shuttle protein (e.g., recombinant LFn-GAL4), wherein the shuttle protein comprises a nucleic-acid-binding domain (for example GAL4) that recognises the double-stranded protein-binding sequence and wherein the shuttle protein is non-covalently bonded to the pair of antisense oligonucleotides.

In another aspect, the present invention provides a system for delivering an antisense oligonucleotide across a membrane of a cell, the system comprising (i) a pair of antisense oligonucleotides, the pair comprising a double-stranded protein-binding sequence (e.g., GAL4) and at least one single-stranded antisense sequence (as shown for example in FIG. 1), and (ii) a shuttle protein having a nucleic-acid-binding domain that is capable of recognising a specific sequence (e.g., CGG-$N_{11}$-CCG) incorporated within the double-stranded protein-binding nucleic acid sequence to non-covalently bind the shuttle protein to the pair of antisense oligonucleotides.

In a further aspect, the present invention provides a method of non-covalently conjugating an antisense oligonucleotide to a shuttle protein (e.g., LFn-GAL4), the method comprising: (i) providing two antisense oligonucleotides, (ii) hybridising the two antisense oligonucleotides to form an antisense hybrid, wherein the antisense hybrid comprises at least one single-stranded antisense sequence and at least one double-stranded protein-binding sequence, (iii) providing a shuttle protein containing a nucleic-acid-binding domain that recognises a double-stranded protein-binding target sequence, and (iv) non-covalently conjugating the shuttle protein to the antisense hybrid by means of the nucleic-acid-binding domain of the protein and the protein-binding sequence of the antisense hybrid.

The method of conjugation and membrane translocation does not require the use of (polycationic or ionic) DNA condensing agents (such as poly(ethylene imine) or poly(L-Lysine)) as these materials are often toxic and this toxicity is thought to be due, at least in part, to their propensity to destabilise cell membranes (Richardson et al., 1999) (and see Table 1 below). In the context of the present invention, a shuttle protein is defined as a protein that is capable of conveying genetic material through a pore in a cell membrane. The pore may comprise a pore-forming protein, such as *Bacillus anthracis* PA83 or PA63.

The oligonucleotides of the invention comprise nucleic acid sequences, which may be of DNA or DNA analogues, for example sulphonated analogues in which certain oxygen atoms are replaced by sulphur. Other DNA analogues that may be found suitable include those disclosed by Leumann (2002). The sequences may directly adjoin each other or be connected by an intervening DNA sequence, preferably at least partly double-stranded.

In a preferred embodiment, the shuttle protein is an attenuated toxin protein. In particular, the shuttle protein may be *B. anthracis* lethal factor domain I (LFn).

Preferably, in the attenuated toxin, at least one toxin domain, e.g., one or more of toxic domains II-IV of the *B. anthracis* lethal factor protein toxin, is replaced by a nucleic-acid-binding domain. For example, the nucleic-acid-binding domain may be *Saccharomyces cerevisiae* GAL4 (fused with LFn).

Advantageously, the antisense oligonucleotide composition further comprises a pore-forming protein. Preferably, the pore-forming protein is a non-toxic protein. One preferred pore-forming protein is *B. anthracis* virulence factor Protective Antigen (PA). In particular, the pore-forming protein may be *B. anthracis* PA83 or PA63.

In one embodiment, (in the instance of targeting syntaxin5 (Syn5) for down-regulation) one of the oligonucleotides includes the antisense sequence 5' AATTTGTTTGTTGAGGCTA 3' (SEQ ID No: 18). Each member of the antisense oligonucleotide pair comprises one of the two complementary strands that hybridise to form the protein-binding sequence (see FIG. 1). The antisense sequence may be downstream (3') or upstream (5') of the protein-binding sequence (or both, if there is more than one antisense sequence in the hybrid that results) (see FIG. 1*a*).

In one embodiment, the protein-binding sequence is CGG-$N_{11}$-CCG where "N" is any nucleotide comprising a purine or pyrimidine base. Suitably, the protein-binding sequence is 5' CGGCTGCTCTGATGCCG 3' (SEQ ID No: 19).

Advantageously, the antisense oligonucleotide composition comprises oligonucleotide pairs that hybridise to form a protein-binding sequence that includes the sequence: 5' CGGCATCAGAGCAGCCG 3' (SEQ ID No: 20). Examples of such sequences are SEQ ID Nos 9, 11 and 13 shown below (Example 4).

In one embodiment, the oligonucleotide further comprises a flanking sequence between the protein-binding sequence and the antisense sequence (see FIG. 1*a*).

Advantageously, the oligonucleotides used in the present invention may be sulphonated, thereby increasing their stability. In sulphonated oligonucleotides, one or more non-bridging oxygen atoms in the oligonucleotide chain may be replaced by sulphur atoms. Sulphonation may be effected by various known methods, for example by use of Beaucage Reagent (3H-1,2-benzodithiole-3-one-1,1,-dioxide) (Cieślak et al., 2005). Other ways of increasing stability of oligonucleotides may be employed in the invention: for example, those disclosed in Leumann (2002).

The present invention also provides an in vitro method of down-regulating the expression of a target gene in the cytosol of a cell by delivering an antisense oligonucleotide across a membrane of the cell using an antisense oligonucleotide composition as described above.

An alternative aspect of the present invention is an antisense oligonucleotide composition as described above for use in a method of down-regulating the expression of a gene from Human Papilloma Virus (HPV) in a human cervical epithelial cell (see FIG. 5 and Example 7). In a further aspect, the present invention provides an antisense oligonucleotide composition as described above as a potential treatment or prophylaxis for cancer, in particular cancers caused by human papilloma virus (HPV), including cervical cancer and oral cancers.

Many plant and bacterial toxins (virulence factors) have evolved to deliver a toxin, in the form of a macromolecular catalytically-active protein domain, to the cytosol of a cell. Examples include cholera toxin (Sandvig et al., 2005), ricin toxin (Sandvig et al., 2010) and anthrax toxin (Gaur et al., 2002). These agents are known to operate in vivo, causing human morbidity and mortality.

The present inventors have prepared a known attenuated version of *Bacillus anthracis* lethal factor (LFn), where the wild-type domains II-IV (responsible for catalytic toxic activity) have been removed using recombinant PCR. These domains (II-IV) have subsequently been replaced with a nucleic-acid-binding domain such as *Saccharomyces cerevisiae* GAL4. All of this is known in the art (Gaur et al., 2002). The inventors have shown that GAL4 can bind, indirectly, to active antisense oligonucleotides under suitable conditions i.e., when two suitable oligonucleotides are hybridised together to form a hybrid containing a single-stranded antisense sequence and a double-stranded (DS) protein-binding sequence. The inventors have further shown that the complete complex (LFn-GAL4::ASO) can be used to translocate antisense oligonucleotides into the cytosol of a cell via interaction with another protein, PA83. Significantly, the processes and materials employed by the inventors to generate the complete antisense oligonucleotide—protein complex mean that condensing agents or polycation affinity handles hitherto regarded as necessary for DNA complex formation in the art (such as poly(L-lysine) (Gaur et al., 2002; WO97/23236), which is toxic and known to destabilise membranes (Richardson et al., 1999)) are not required.

A preferred embodiment of a system in accordance with the present invention provides a single-stranded antisense oligonucleotide sequence 3' and/or 5' to a double-stranded (DS) protein-binding sequence. Proteins such as LFn may be used in conjunction with pore-forming proteins, for example PA83. PA83 has the capacity to enhance the membrane translocation of LFn. The interaction between LFn and PA83 is described elsewhere (Krantz et al., 2005) though it has been documented to require the molten-globular transition of cargo during pore translocation. We have now shown that it is possible to use a supramolecular assembly as cargo and that an antisense sequence associated with that supramolecular assembly can translocate into the cytosol. This could not have been predicted.

The inventors have further developed the system to use hybridised oligonucleotide containing a double-stranded LFn-GAL4 binding sequence and a 3' and/or 5' overhanging single-stranded antisense sequence, which they have shown to be no less effective than the antisense (single-stranded nucleotide) sequence without any flanking sequence at antisense oligonucleotide (ASO) concentrations above 30 pMol. The complex developed by the inventors can be used as an antisense oligonucleotide conjugation system to facilitate antisense oligonucleotide cytosolic delivery without a covalent attachment between the oligonucleotides and the LFn-GAL4 protein. The present invention provides a useful tool for in vitro research as well as a basis for an antisense oligonucleotide pharmaceutical composition and a critical part of the delivery methodology of any suitable antisense therapy. In particular, the present invention may form the basis for an antisense antiviral composition for the treatment of HPV-infected cervical epithelial cells.

The dimerisation of the LFn-GAL4 protein in response to the presence of a double-stranded protein-recognition nucleic acid sequence adjacent to the antisense sequence has been shown using small-angle neutron scattering (SANS) (see Example 5). Example 5 shows that the protein LFn-GAL4 forms high molecular weight complexes (protein radius of gyration ($R_g$) expanding from approximately 5 nm to 25 nm) upon the addition of the hybrid oligonucleotide compositions of the invention.

In order to test a three-component system in accordance with the present invention, the inventors initially produced a prototype. The system's ability to down-regulate genes was tested in human epithelial cells (Hela). The LFn-GAL4:: oligonucleotide composite, when mixed with PA83 facilitates the down-regulation of the specific, selected gene (see Example 6), corresponding to the antisense sequence. With reference to Example 6, this illustrates the down-regulation of the protein Syntaxin5 by Western blotting and immuno-detection (Suga et al., 2005). Gene specificity (as well as controlling for cell number) is further emphasised by normalising the levels of target gene expression to the expression levels of a "housekeeper" gene such as Derlin1 and through the inclusion of "non-sense" controls (see FIG. 4). 'Non-sense' controls are controls that include single-stranded DNA that is not complementary to target RNA in the gene being expressed, and accordingly are not expected to inhibit its expression.

In addition antisense activity is also shown against the expression of the HPV gene E7 (see Example 7). HPV E7 is critical to the propagation of the HPV viral life cycle and is a target for therapeutic intervention (Jonson et al., 2008).

The arrangement of two oligonucleotide strands to provide a double-stranded protein-binding region or sequence, whilst leaving free single-stranded regions of sequence that have antisense activity provides a convenient conjugation method that can be used to bind the antisense domains to agents already described in the art (such as LFn-GAL4 and PA83). This facilitates the cytosolic delivery of the antisense agents that can mediate the down-regulation of genes coding for potential drug targets, for example HPV E7.

Specific embodiments to the invention are now described in more detail with reference to the accompanying drawings, in which:

FIG. 1 comprises FIGS. 1a to 1e showing five different compositions according to the invention, illustrating different topologies for creating a double-stranded protein-binding site from a pair of single-stranded antisense oligonucleotides;

FIG. 2 compares inhibitory activity of a composition according to the invention with other antisense compositions in a cell-free assay.

FIG. 3, by using small-angle neutron scattering (SANS), shows that in the presence of antisense compositions of the invention, LFn-GAL4 dimerise to form compositions of higher molecular weight.

FIG. 6 is the LFn-GAL4 nucleotide sequence (SEQ ID No: 1);

FIG. 7 is the LFn (LF domain I) protein sequence (SEQ ID No: 2);

FIG. 8 is the GAL4 (amino acids 1-147) protein sequence (SEQ ID No: 3);

FIG. 9 is the V5-LFn-GAL4-6His DNA sequence (SEQ ID No: 4);

FIG. 10 is the V5-LFn-GAL4-6His protein sequence (SEQ ID No: 5);

FIG. 11 is the MRGS-6His-PA83 DNA sequence (SEQ ID No: 6); and

FIG. 12 is the MRGS-6His-PA83 protein sequence (SEQ ID No: 7).

EXAMPLE 1: FORMATION OF SHUTTLE PROTEIN

Figure 1:
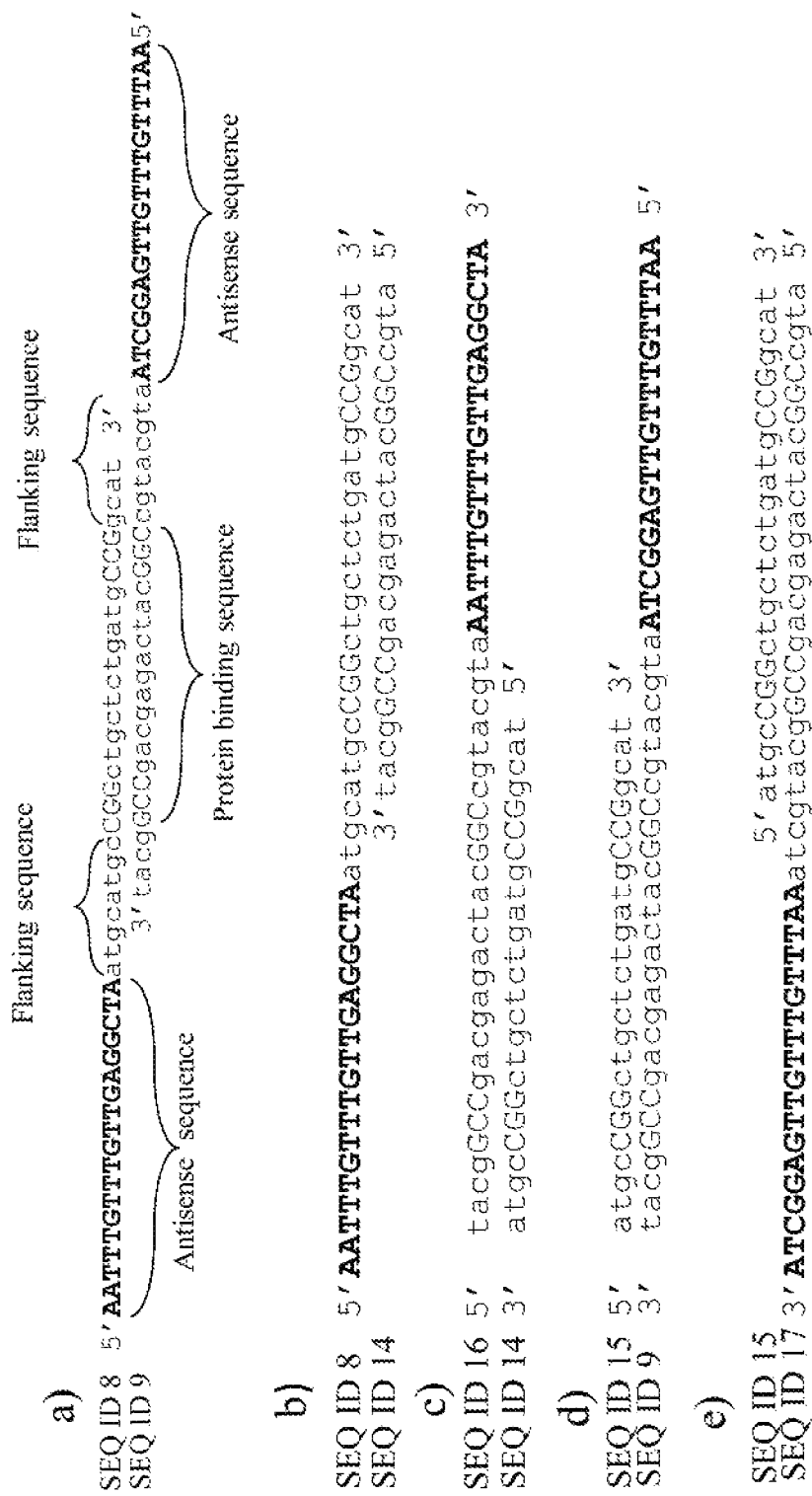

LFn-GAL4 was enriched from cultures of *E. coli* with a yield of approximately 5 mg/l. The DNA sequence coding for the protein LFn-GAL4 is SEQ ID No: 4 (FIG. 9). This sequence is within the plasmid pET151/D (Invitrogen), an *E. coli* expression cassette.

The DNA sequence for LFn (LF domain 1) and GAL4 (amino-acids 1-147) (known in the art—Gaur et al., 2002) was sub-cloned into the pET151/D bacterial expression cassette. The addition of a V5 epitope tag at the N-terminus and 6× histidine affinity tag at the C-terminus allowed for the rapid immunodetection and affinity purification, respectively, of the fusion protein from bacterial lysate.

Recombinant protein production: Chemically competent bacteria (*E. coli* BL21*DE3 (Invitrogen)) were transformed with purified plasmid (described above) and cultured overnight (10 mL) in 2× yeast extract tyrptone (2×YT) bacterial culture, containing ampicillin (200 µg/ml) media prior to sub-culturing in large volumes (1 L) of 2×YT also containing a similar concentration of ampicillin. Bacterial cultures were then incubated in an orbital shaker set at 180 rpm (at 37° C.) for 3 hours. Subsequently isopropyl β-D-1-thiogalactopyrnoside (IPTG) was added to a final concentration of 500 µM and incubated for a further 3 hours. Bacterial pellets were prepared by centrifugation (6 000×g for 10 min at 4° C.) and subject to lysis using a French Press set to 1500 PSI. Bacterial lysates were subjected to further centrifugation (20 000×g for 20 min). The resultant supernatant was passed over a 6×His (Co$^{2+}$ Tallon® resin (Clontech)) affinity chromatography column. LFn-GAL4 was eluted using 150 mM imidazole in fractions of 1 mL. Fractions were analysed for protein purity and concentration, pooled and dialysed in phosphate buffered saline. The final protein preparation was evaluated by SDS-PAGE and subjected to Coomassie staining (to determine protein purity) and Western blot analysis (using an antibody specific to V5 and 6×His).

EXAMPLE 2: PRODUCTION OF PORE-FORMING PROTEIN

PA83 was enriched from cultures of E. coli BL21*DE3 with a yield of approximately 5 mg/l. A plasmid containing the known DNA sequence encoding PA83 was obtained as a gift from Professor Les Baillie (University of Cardiff). It contained the PA83-encoding sequence sub-cloned into the bacterial expression vector pQE30 providing an N-terminal 6× histidine affinity tag (Baillie et al., 2010). Chemically competent bacteria were transformed with purified plasmid and cultured overnight as before. During the growth phase, the 1 l bacterial cultures were incubated in an orbital shaker set at 180 rpm (at 37° C.) for 3 hours. Subsequently IPTG was added to a final concentration of 500 µM and incubated for a further 2 hours. Bacterial pellets were prepared by centrifugation (6 000×g for 10 min) and subjected to lysis using a French Press as before. Bacterial lysates were subjected to further centrifugation (20 000×g for 20 min). The resultant supernatant was passed over a 6× histidine affinity chromatography column. PA was eluted using 150 mM imidazole in fractions of 1 mL. Protein fractions were analysed for purity and concentration, pooled, and dialysed in phosphate-buffered saline (PBS). The final protein preparation was evaluated by SDS-PAGE and subjected to Coomassie staining (to determine purity) and western blot analysis (using an antibody specific to PA).

The amino-acid sequence for PA83 is shown in SEQ ID No: 7 (FIG. 12—MRGS-6His-PA83 protein).

EXAMPLE 3: FORMATION OF ANTISENSE OLIGONUCLEOTIDE WITH DOUBLE-STRANDED PROTEIN-BINDING REGION

Two complementary oligonucleotides, each encoding one strand of a GAL4 recognition sequence, were annealed, to form a double-stranded (GAL4) protein-binding sequence with flanking single-stranded antisense sequences. The ASO compositions described (SEQ ID Nos: 8 & 9: see Example 4) were used in this instance. The resulting composition is shown in FIG. 1a. Antisense oligonucleotide hybridization was performed by repeated (×10) thermal cycling, melting (1 min. at 94° C.) and re-annealing (1 min. at 55° C.) the two partially overlapping oligonucleotides, leaving single-strand antisense oligonucleotide sequence free to interact with mRNA in a sequence-specific manner.

FIGS. 1a-1e show several possible topologies of the protein-binding (DS) sequence of DNA (or DNA analogues) in relation to the antisense nucleic acid sequence(s) using the protein::oligonucleotide conjugation strategy disclosed herein. FIG. 1a shows two sequences SEQ ID Nos: 8 and 9 oriented in opposite senses and bonded together by complementary sections—bases 23 to 48 in SEQ ID No: 8 bonding with bases 48 to 23 of SEQ ID No. 9 (SEQ ID No. 9 is shown 3' to 5' in FIG. 1a). The ASO hybrids of our invention may or may not include an additional DNA sequence flanking the antisense sequence(s). As shown in FIGS. 1a-1e, the double-stranded (protein-binding) region of the ASO hybrid can be formed in a number of different ways. For example, the double-stranded region can be positioned between two antisense sequences (which may be identical or different), as in FIG. 1a. Alternatively, the double-stranded region can be positioned at one side of a single antisense oligonucleotide, as in FIGS. 1b-1e.

EXAMPLE 4: PRODUCTION OF DNA SEQUENCES USEFUL FOR INHIBITING EXPRESSION OF SPECIFIC PROTEINS

Antisense Oligonucleotide Sequence Specific for Syntaxin5 with Flanking and GAL4 Binding Sequence:

```
Forward oligonucleotide
                                        (SEQ ID No: 8)
5' AATTTGTTTGTTGAGGCTAATGCATGCCGGCTGCTCTGAT
GCCGGCAT 3'

Reverse oligonucleotide
                                        (SEQ ID No: 9)
5' AATTTGTTTGTTGAGGCTAATGCATGCCGGCATCAGAGCA
GCCGGCAT 3'
```

Antisense Oligonucleotide Sequence Specific for HPV (Serotype 18) Early (E) 7 mRNA Transcripts, with Flanking and GAL4 Binding Sequence:

```
Forward oligonucleotide
                                       (SEQ ID No: 10)
5' GGTCGTCTGCTGAGCTTTCTATGCATGCCGGCTGCTCTGA
TGCCGGCAT 3'

Reverse oligonucleotide
                                       (SEQ ID No: 11)
5' GGTCGTCTGCTGAGCTTTCTATGCATGCCGGCATCAGAGC
AGCCGGCAT 3'
```

Antisense Oligonucleotide Sequence Specific for TurboGFP mRNA Transcripts, with Flanking and GAL4 Binding Sequence:

```
Forward oligonucleotide
                                       (SEQ ID No: 12)
5' GGTGCTCTTCATCTTGTTGGTATGCATGCCGGCTGCTCTG
ATGCCGGCAT 3'

Reverse oligonucleotide
                                       (SEQ ID No: 13)
5' GGTGCTCTTCATCTTGTTGGTATGCCGGCATCAGAGCAGC
CGGCATGCAT 3'
```

The above oligonucleotides (SEQ ID Nos: 8-13) were synthesised with phosphorothioate modification to enhance the lifetime of the antisense oligonucleotide.

Forward and reverse primer pairs (SEQ ID Nos 8 with 9; 10 with 11; 12 with 13) were hybridized using a PCR cycler using the following conditions: Heated to 94° C. for 1 min., and cooled to 55° C. for 1 min., ×10. This annealing process produced hybrid single- and double-stranded DNA sequences according to the invention.

EXAMPLE 5: FORMATION OF AN ANTISENSE OLIGONUCLEOTIDE-SHUTTLE (LFN-GAL4) COMPLEX

Annealed ASO hybrids were produced (as in Example 4). These ASO hybrids were co-incubated with LFn-GAL4 in phosphate-buffered saline (PBS) for 30 min at room temperature at the appropriate stoichiometry (i.e., at approximately a 3:1 protein to oligonucleotide molar ratio).

Figure 3:
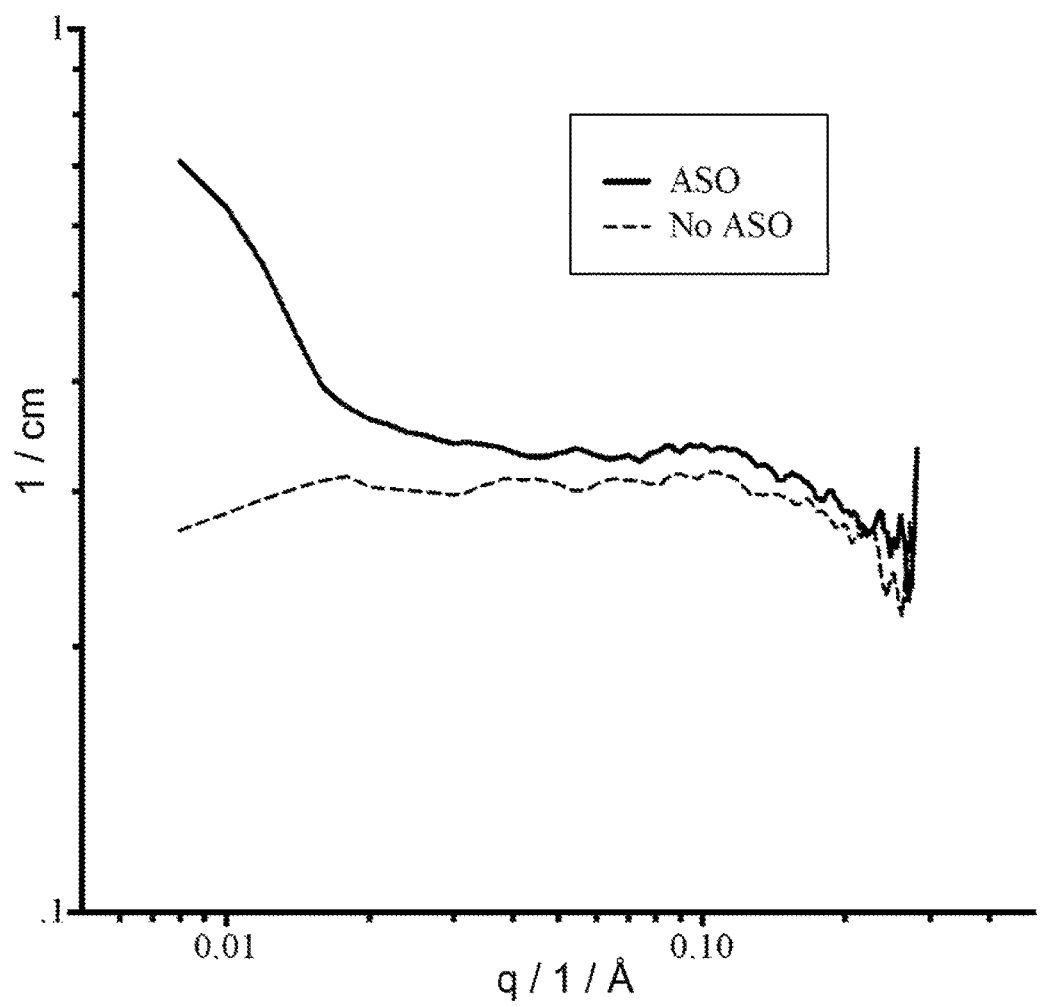

One such product so obtained was investigated by small-angle neutron scattering (SANS). The profile resulting is compared in FIG. 3 with that obtained in the absence of any antisense oligonucleotide. FIG. 3 shows LFn-GAL4 dimerisation as measured by SANS in response to the addition of the antisense oligonucleotide composition shown in FIG. 1a—small angle neutron scattering by LFn-GAL4 and LFn-GAL4::DS-antisense oligonucleotide in PBS (at approximately 0.5 mg/ml of LFn-GAL4 in each instance). Units of the x-axis of FIG. 3 are q/l/angstrom and of the y-axis are 1/cm. The upper thick black line shows results in the presence of the ASO, in comparison with the lower thin line where the ASO is absent. The differential in scattering profile between 0.01 and 0.04 (q/1/Å) is attributable to the LFn-GAL4 dimerising, caused by association with the double-stranded protein-binding sequence forming part of the oligonucleotide (FIG. 1a). In this instance 2 mm cuvettes (Hellman Analytics, Essex, UK) were loaded with LFn-GAL4 and LFn-GAL4::oligonucleotide stoichiometry of 3:1 respectively (molar ratio).

The intensity of such scattered radiation is a reflection of the scatterer size and shape, as well as composition (i.e., LFn-GAL4). Both the individual proteins and their blends were examined. For the individual components, generally no scattering was observed, indicating their relatively small size. In the mixture of LFn-GAL4 and the hybridised oligonucleotide, scattering was observed, confirming that an interaction was occurring to form larger structures (i.e., LFn-GAL4::ASO complexes).

EXAMPLE 6: DOWN-REGULATION OF TARGET GENE EXPRESSION (SYNTAXIN5)

One of the complexes produced in Example 5 was employed to target the expression of the gene Syntaxin5 in Hela cells. The pore-forming protein PA83 was used to help mediate antisense oligonucleotide membrane translocation via an interaction with LFn-GAL4. The ASO portion of the complex consisted of two annealed (as in Example 4) ASO sequences (SEQ ID Nos: 8 & 9). Hela cells produce Syntaxin5 when cultured under normal conditions. Hela cells were treated in various ways at a range of ASO complex concentrations: 0 (control), 1, 10, 50, 100 and 200 pMol per liter.

Figure 4:
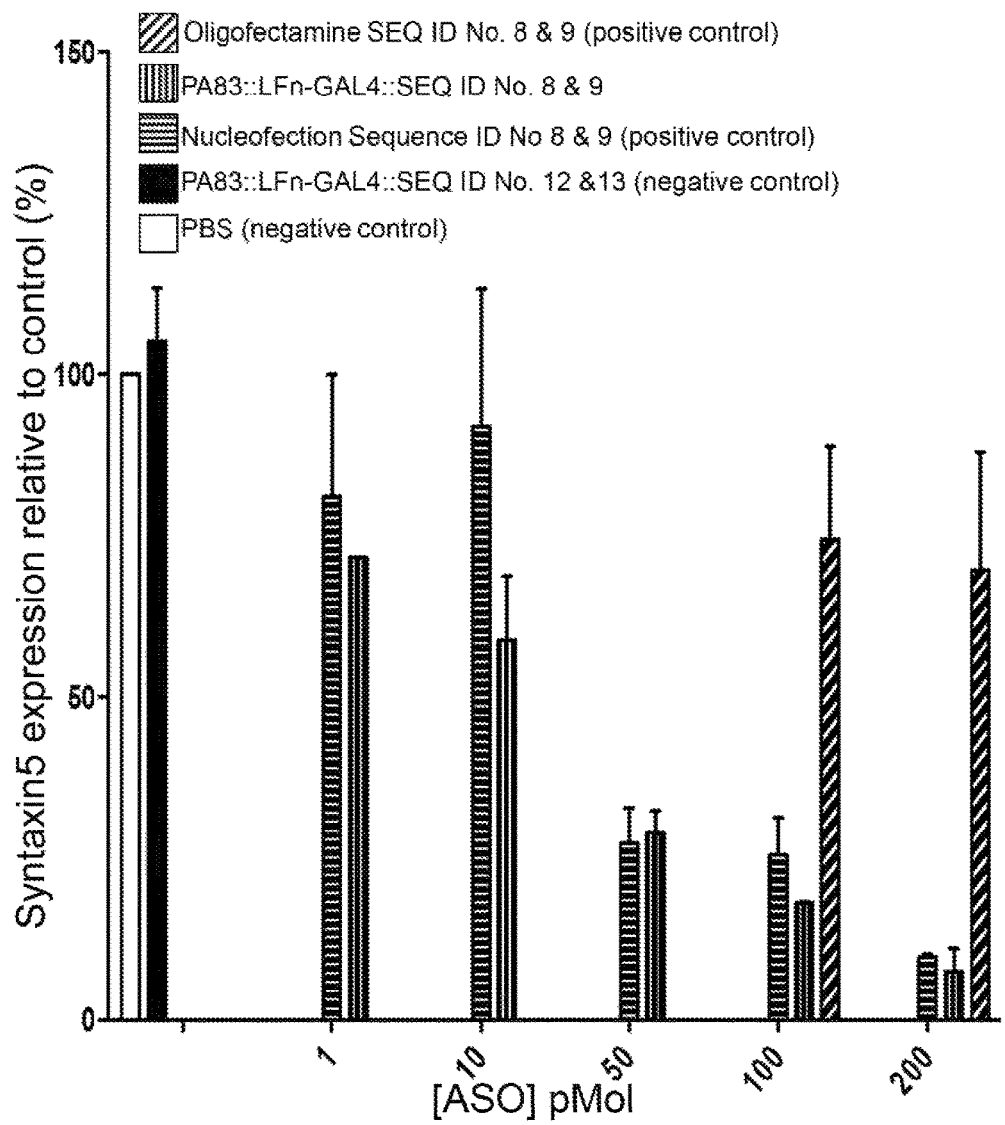
FIGS. 4 and 5 illustrate how the described system can down-regulate expression of two different genes: down-regulating the expression of Syntaxin5 is shown in FIG. 4 and of HPV (serotype 18) Early (E)7 is shown in FIG. 5.

In FIG. 4: the black filled bar represents Hela cells treated with PA83, LFn-GAL4 and a "non-Syntaxin5" (GFP specific) ASO (formed from hybridised SEQ ID No:12 and 13). The bar with no fill represents Hela cells treated with PBS only. These two treatments show sequence specificity for Syntaxin5 down-regulation (since the anti-GFP ASO sequence here is inactive against Syntaxin5) and serve as negative controls. Bars filled with horizontal hatching represent Hela cells electroporated with hybrid ASO specific for Syntaxin5 (formed from SEQ ID Nos: 8 and 9). Bars filled with vertical hatching represent Hela cells treated with PA83, LFn-GAL4 and hybrid ASO specific for Syntaxin5 (formed from SEQ ID Nos: 8 and 9). The bars filled with diagonal hatching represent Hela cells treated with hybrid ASO specific for Syntaxin5 (formed from SEQ ID Nos: 8 and 9) mixed with Oligofectamine (Invitrogen), following the manufacturer's recommendations.

Syntaxin5 expression levels in the cells were measured after 24 hours using immunoblotting. Results are shown as % expression of control (Hela cells treated with PBS only) (y axis). The data show that compositions according to the invention down-regulate Syntaxin5 expression in a gene-specific manner. This is shown at a population level by Western blotting and immunodetection. The graph of FIG. 4 displays Syntaxin5 expression levels and shows the effect of loading antisense oligonucleotide hybrids (3.2 μg/mL) (SEQ ID Nos: 8 and 9) onto LFn-GAL4 (50 μg/mL) co-incubated with PA (50 μg/mL) on Hela cells relative to the expression of a housekeeper gene, Derlin1 (to control for any variation in cell number). The data shown is derived from 3 separate experiments and demonstrates that the addition of the compositions described can mediate the knockdown of a specific gene antisense oligonucleotide encoding an antisense sequence (i.e., Syntaxin5). The data represent three repeats of each experiment and the error bars represent the standard error of the mean.

EXAMPLE 7: DOWN-REGULATION OF TARGET GENE EXPRESSION (HPV18 E7)

Figure 5:
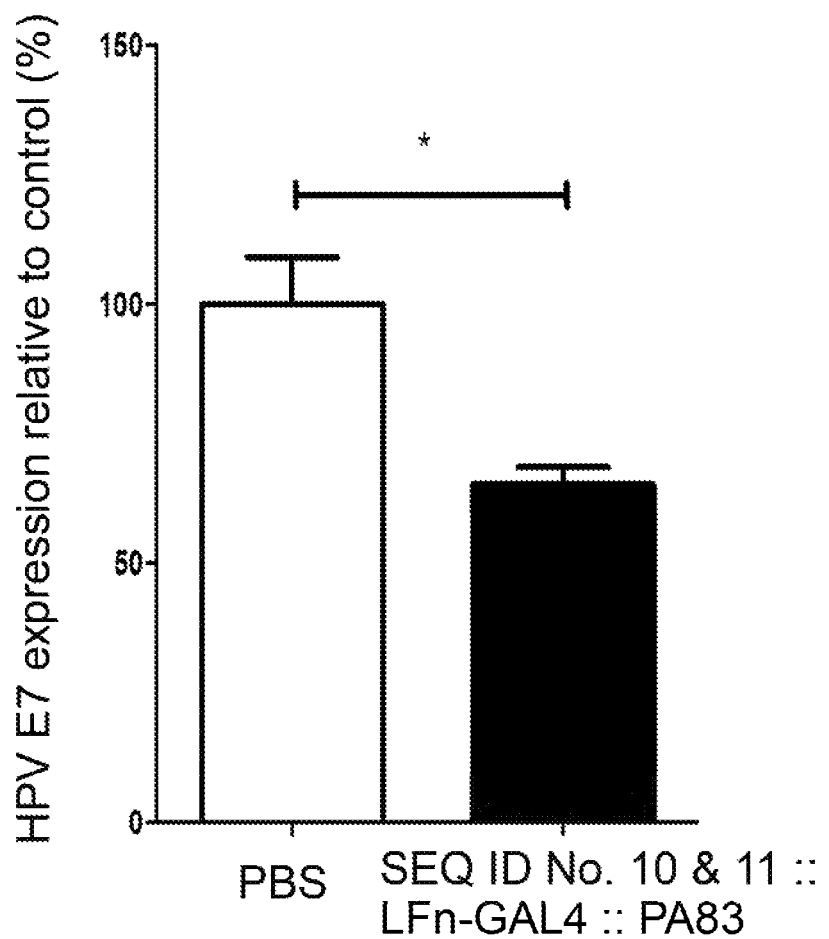

An experiment to examine the efficacy of anti-HPV E7 antisense oligonucleotides against the expression of Human Papilloma Virus (serotype 18) Early 7 in Hela cells was undertaken as described in Example 6 above, but using different oligonucleotide sequences. In this instance the Syntaxin5-specific ASO hybrids (formed from SEQ ID No: 8 and SEQ ID No: 9) of Example 6 were replaced with HPV-E7-specific ASO hybrid also containing the hybrid protein-binding region and a small flanking region (formed from SEQ ID No:10 and SEQ ID No:11). In this example 200 pM of oligonucleotide, associated with LFn-GAL4 and PA83, was used (this is the black bar on the graph in FIG. 5). The result is shown in FIG. 5: % gene expression is shown on the y axis. The control treatment, PBS, is taken as 100%: this is the white bar on the graph in FIG. 5. The data represent three repeats of each experiment and the error bars represent the standard error of the mean. There was a statistical difference between the two treatments (p=0.0104 as measured by a one-tailed, unpaired t-test).

EXAMPLE 8: IN VITRO TOXICITY OF COMPOSITIONS OF THE INVENTION COMPARED WITH POLY(ETHYLENEIMINE)

The ASO hybrid-shuttle complexes produced as in Example 5 were tested for toxicity in relation to poly (ethyleneimine) (PEI) (Table 1). These data show a differential in toxicity relative to cells exposed to varying concentrations of either PEI, a cationic polymer well characterised in the literature as being able to mediate transfection, and LFn-GAL4 protein after hybridisation with ASO hybrids in the presence of 50 m/mL PA over 72 h. Cell viability was normalised to untreated cells and measured by the addition of MTT (Richardson et al., 1999).

TABLE 1

|  | IC$_{50}$ in HeLa (micrograms/ml) | IC$_{50}$ in Vero (micrograms/ml) |
| --- | --- | --- |
| 25 KDa Branched PEI | 2.9 +/− 0.6 | 7.3 +/− 0.1 |
| 0.8 KDa Branched PEI | 2.4 +/− 0.2 | 7.4 +/− 0.3 |
| 20 KDa Linear PEI | 3.0 +/− 0.1 | 6.9 +/− 0.5 |
| PA83 | >100 | >100 |
| ASO | >100 | >100 |
| GAL4-LFn | >100 | >100 |
| ASO ::GAL4-LFn + PA83 | >100 | >100 |

EXAMPLE 9: ANTISENSE INHIBITION OF AN IN VITRO TRANSLATION ASSAY USING DIFFERENT ANTISENSE OLIGONUCLEOTIDE COMPOSITIONS

Figure 2:
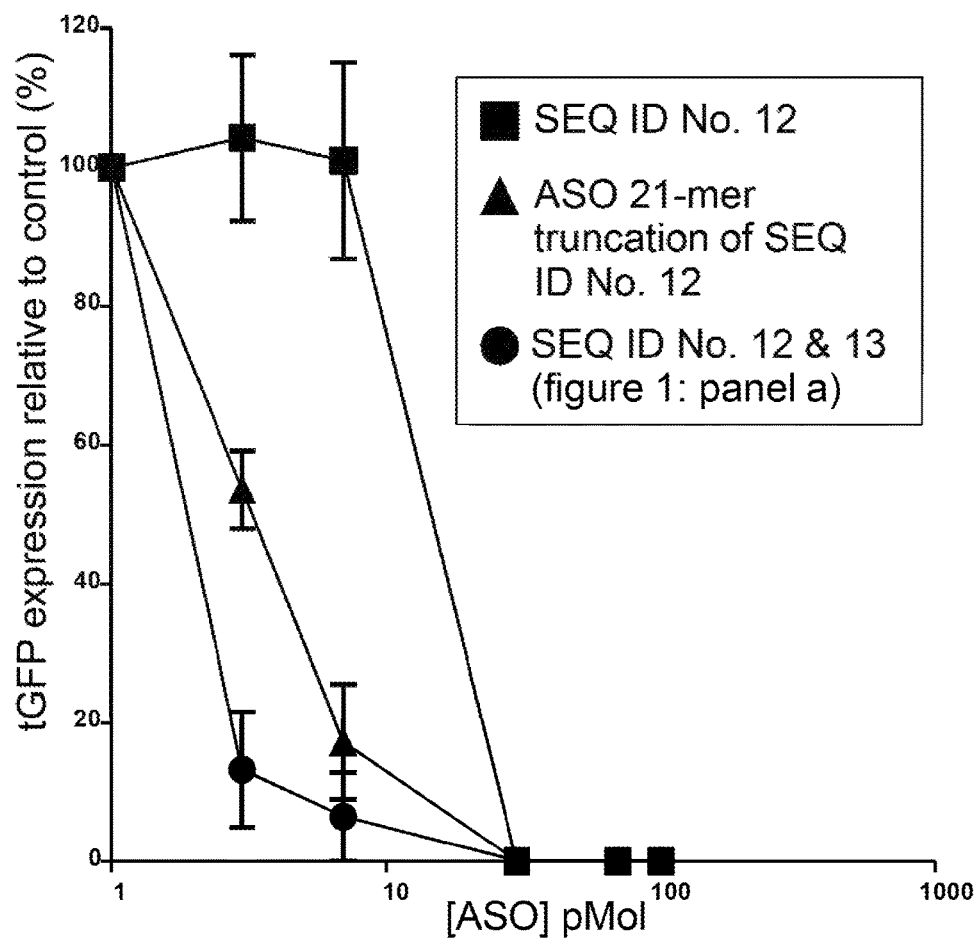

FIG. 2 shows the effect of compositions of the invention as compared with component ASOs in a cell-free assay (where membrane translocation is not rate-limiting).

Control reactions were performed using a "One step human high yield mini- in vitro translation kit" (Thermo Scientific), in conjunction with a control plasmid encoding the protein turboGFP (green fluorescent protein—Evrogen). The reactions were performed in 4.5 µl volumes (incubated for 3 h at 30° C.) and the expression of turboGFP was monitored by Western immunoblotting using an anti-6His primary antibody (1:1000 dilution) and an anti-mouse HRP-conjugated secondary antibody (1:1000). Detection was performed using a Picostable ECL kit (GE Healthcare). Three anti-turbo GFP antisense oligonucleotide (ASO) compositions were added to the reaction at differing concentrations at the beginning of the 3 h incubation period previously described.

Results are shown in FIG. 2, (n=3±SEM) relative to a control containing no antisense oligonucleotides. In FIG. 2 the y-axis represents the expression of turboGPF (%) relative to an untreated control, while the x-axis represents concentration of antisense oligonucleotide added to the reaction (in pMol). The data points represented with a square were derived from a single-stranded ASO oligonucleotide, SEQ ID No: 12, consisting of the turboGPF antisense sequence and (one strand of the) protein-binding sequence. The data points represented by triangles represent data generated from only the antisense sequence incorporated into SEQ ID No: 12 (i.e., the 21-mer GGTGCTCTTCATCT-TGTTGGA, SEQ ID No: 21). The data points represented by circles were generated from the ASO hybrid of the invention formed by annealing together SEQ ID Nos: 12 and 13. The results shown in FIG. 2 illustrate that (in vitro) the presence of the protein-binding sequence in the ASO hybrid does not inhibit the activity of the antisense sequence above an ASO concentration of 30 pMol.

Our invention may be used to produce antisense compositions having substantially no significantly reduced antisense activity (as measured in cell-free assay), relative to an antisense control having no protein-binding sequence or flanking sequence, at or above a 30 pMol concentration of antisense oligonucleotide (ASO). Example 9 above (FIG. 2) illustrates this.

REFERENCES

Baillie L. W. (2009) Is new always better than old?: The development of human vaccines for anthrax. *Hum Vaccine*, 5(12):806-16.

Baillie L. W., Huwar T. B., Moore S., Mellado-Sanchez G., Rodriguez L., Neeson B. N., Flick-Smith H. C., Jenner D. C., Atkins H. S., Ingram R. J., Altmann D. M., Nataro J. P., and Pasetti M. F. (2010) An anthrax subunit vaccine candidate based on protective regions of *Bacillus anthracis* protective antigen and lethal factor. *Vaccine,* 28(41), pp. 6740-6748.

Biroccio A., Leonetti C., and Zupi G. (2003) The future of antisense therapy: combination of anticancer treatments. *Oncogene,* 22:6579-6588.

Campbell R. N., Leverentz M. K., Ryan L. A., Reece R. J. (2008). Metabolic control of transcription: Paradigms and lessons from *Saccharomyces cerevsiae. Biochem J.* 414 (2):177-87.

Cieślak J., Ausin C., Chmielewski M. K., Kauffman J. S., Snyder J., Del-Grosso A., Beaucage S. L. (2005) NMR study of the desulfurization of oligonucleoside phosphorothioates effected by "aged" trichloroacetic acid solutions. *J. Org. Chem.* 70(8):3303-6.

Gaur R., Gupta P. K., Goyal A., Wiles W., and Singh Y. (2002) Delivery of nucleic acid into mammalian cells by anthrax toxin. *Biochemical and Biophysical Research Communications.* 297:1121-1127.

Jonson A. L., Rogers L. M., Ramakrishnan S. and Downs Jr L. S. (2008), Gene silencing with siRNA targeting E6/E7 as a therapeutic intervention in a mouse model of cervical cancer. *Gynecologic Oncology.* 111(2): 356-364.

Kim S. H., Mok H., Jeong J. H., Kim S. W., Park T. G. (2006) Comparative evaluation of target-specific GFP gene silencing efficiencies for antisense CDN, synthetic siRNA, and siRNA plasmid complexed with PE1-PEG-FOL conjugate. *Bioconjug Chem.* 17(1):241-4.

Krantz B. A., Melnyk R. A., Zhang S., Juris S. J., Lacy D. B., Wu Z., Finkelstein A., Collier R. J., (2005) A phenylalanine clamp catalyzes protein translocation through the anthrax toxin pore *Science.* 309(5735):777-81.

Kushner N., Zhang D., Touzjian N., Essex M., Lieberman J., and Lu Y. (2003) A Fragment of Anthrax Lethal Factor Delivers Proteins to the Cytosol without Requiring Protective Antigen. *Proc Natl Acad Sci USA,* 100 (11): 6652-6657.

Leumann C., DNA analogues: from supramolecular principles to biological properties. (2002) *Bioorg. Med Chem.;* 10(4):841-54.

Lysik M. A., Wu-Pong S. (2003) Innovations in oligonucleotide drug delivery. *J. Pharm. Sci.* 92:1559-1573.

Parkin, D M. (2006) The global health burden of infection-associated cancers in the year 2002. *Int. J. Cancer.* 118:3030-3044.

Richardson S., Ferruti P. and Duncan R. (1999) Poly(amidoamine)s as potential endosomolytic polymers: Evaluation in vitro and body distribution in normal and tumour bearing animals. *J. Drug Targeting,* 6(6), 391-404.

Roehr B, (1998) Fomivirsen approved for CMV retinitis. *J. Int. Physicians AIDS Care.* 4(10): 14-6.

Sandvig K., and van Deurs B. (2005). Delivery into cells: Lessons learned from plant and bacterial toxins. *Gene Therapy*. (12)s 865-872.

Sandvig, Kirsten; Torgersen, Maria Lyngaas; Engedal, Kim Nikolai; Skotland, Tore & Iversen, Tore Geir (2010). Protein toxins from plants and bacteria: Probes for intracellular transport and tools in medicine. *FEBS Letters.* 584(12)s 2626-2634.

Suga K. Hattori H. and Saito A. (2005). RNA interference-mediated silencing of the syntaxin 5 gene induces Golgi fragmentation but capable of transporting vesicles. *FEBS Letters.* 579(20):4226-4234.

U.S. Patent WO97/23236: The use of toxin peptides and/or affinity handles for delivering compounds into cells.

Yacyshyn B. R., Bowen-Yacyshyn M. B., Jewell L., Rothlein R. A., Mainolfi E., Tami J. A., Bennett C. F., Kisner D. L., and Shanahan W. R. (1998) A placebo-controlled trial of ICAM-1 antisense oligonucleotide in the treatment of steroid-dependent Crohn's disease. *Gastroenterology.* 114:1133-1142.

Zornetta I., Brandi L., Janowiak B., Dal Molin F., Tonello F., Collier J. and Montecucco C. (2010) Imaging the cell entry of the anthrax oedema and lethal toxins with fluorescent protein chimeras, *Cellular Microbiology,* 12(10); 1435-45.

The invention claimed is:

1. A pharmaceutically acceptable antisense oligonucleotide composition useful for delivering antisense oligonucleotide into the cytosol of a cell, comprising a complex formed from:
   (i) a pair of partially complementary, single-stranded oligonucleotides hybridized to give at least one single-stranded antisense sequence and at least one double-stranded protein-binding sequence; and
   (ii) a shuttle protein capable of conveying genetic material through a pore in a cell membrane, the shuttle protein comprising a nucleic-acid-binding domain that recognizes the double-stranded protein-binding sequence and is non-covalently bound thereto;
   wherein the shuttle protein is an attenuated toxin protein or a protein homologous thereto, in which said attenuated toxin protein or homologous protein at least one toxin domain has been replaced by a said nucleic acid binding domain;
   and wherein the composition further comprises:
   (iii) a pore-forming protein which is capable of interaction with the said complex to facilitate translocation of the complex into the cytosol of the cell.

2. A composition of claim 1, comprising an oligonucleotide that is modified by sulfonation to increase stability.

3. An antisense oligonucleotide composition as claimed in claim 1, wherein the protein-binding sequence is CGG-$N_{11}$-CCG, where "N" is any purine or pyrimidine base.

4. An antisense oligonucleotide composition as claimed in claim 1, wherein the protein-binding sequence is:
   5'-CGGCTGCTCTGATGCCG-3' (SEQ ID NO: 19) or
   5'-CGGCATCAGAGCAGCCG-3' (SEQ ID NO: 20).

5. An antisense oligonucleotide composition as claimed in claim 1, wherein the shuttle protein is homologous with an attenuated toxin protein.

6. An antisense oligonucleotide composition as claimed in claim 5, wherein the shuttle protein contains *B. anthracis* lethal factor (LF) domain I (LFn).

7. An antisense oligonucleotide composition as claimed in claim 6, wherein at least one of domains (II-IV) of LF is replaced by the nucleic-acid-binding domain.

8. An antisense oligonucleotide composition as claimed in claim 1, wherein the nucleic-acid-binding domain of the shuttle protein is *Saccharomyces cerevisiae* GAL4.

9. An antisense oligonucleotide composition as claimed in claim 1 in which the pore-forming protein is *B. anthracis* virulence factor Protective Antigen PA83.

10. An antisense oligonucleotide composition as claimed in claim 1, in which the antisense sequence is single-stranded DNA designed to hybridize to messenger RNA derived from a target gene.

11. An antisense oligonucleotide composition as claimed in claim 10 in which the target gene is expressed by a virus.

12. An antisense oligonucleotide composition as claimed in claim 11 in which the target gene is expressed by Human Papilloma Virus (HPV).

13. A method of transporting an antisense oligonucleotide across a membrane of a cell, the method comprising: providing an antisense oligonucleotide composition as claimed in claim 1, and applying the antisense oligonucleotide composition to the cell.

14. A method of treating a subject infected with Human Papilloma Virus or having cervical cancer, comprising applying to the subject a therapeutically effective amount of a composition as claimed in claim 12, whereby the composition is pharmaceutically acceptable.

* * * * *